US012685858B2

(12) United States Patent (10) Patent No.: US 12,685,858 B2
Linehan et al. (45) Date of Patent: Jul. 21, 2026

(54) DIMENSIONALLY ADJUSTABLE EXTRACORPOREAL LIFE SUPPORT CANNULA

(71) Applicant: CardiacAssist, Inc., Pittsburgh, PA (US)

(72) Inventors: Michael J. Linehan, Pittsburgh, PA (US); Robert G. Svitek, Freeport, PA (US)

(73) Assignee: CardiacAssist, Inc.

( * ) Notice: Subject to any disclaimer, the term of this patent is extended or adjusted under 35 U.S.C. 154(b) by 883 days.

(21) Appl. No.: 17/815,710

(22) Filed: Jul. 28, 2022

(65) Prior Publication Data

US 2024/0033499 A1 Feb. 1, 2024

(51) Int. Cl.
*A61M 25/00* (2006.01)
*A61M 60/845* (2021.01)
(52) U.S. Cl.
CPC ... *A61M 60/845* (2021.01); *A61M 2025/0004* (2013.01); *A61M 25/007* (2013.01); *A61M 2210/125* (2013.01)
(58) Field of Classification Search
CPC .............. A61M 60/845; A61M 25/007; A61M 2025/0004; A61M 2210/125; A61M 1/3659; A61M 1/3666; A61M 2025/0024; A61M 2025/0031; A61M 25/003; A61M 25/00; A61M 2025/0058; A61M 25/0105; A61M 25/0127; A61M 25/0158; A61M 2025/0161; A61M 25/0074
See application file for complete search history.

(56) References Cited

U.S. PATENT DOCUMENTS

| 3,851,646 | A | 12/1974 | Sams |
| 3,902,492 | A | 9/1975 | Greenhalgh |
| 4,248,224 | A | 2/1981 | Jones |
| 4,309,994 | A | 1/1982 | Grunwald |
| 4,804,359 | A | 2/1989 | Grunwald et al. |
| 4,969,890 | A | 11/1990 | Sugita et al. |
| 5,476,453 | A | 12/1995 | Mehta |

(Continued)

FOREIGN PATENT DOCUMENTS

| GB | 2575882 A | 1/2020 |
| WO | 9960267 A1 | 11/1999 |

*Primary Examiner* — Adam Marcetich
(74) *Attorney, Agent, or Firm* — Seager, Tufte & Wickhem LLP

(57) ABSTRACT

A cannula for an ECLS system may include a tubular member and an actuatable structure. The actuatable structure may be responsive to an external stimulus such that an inner diameter of the tubular member changes as the external stimulus changes. A system may include the cannula and a controller in electrical communication with the actuatable structure. The controller may be user-configurable to set a desired value for an inner diameter of the tubular member. A method of connecting a patient's vasculature to an ECLS system may include advancing a delivery sheath into the vasculature, moving the delivery sheath relative to the cannula to expose the cannula within the vasculature, and shifting the actuatable structure from a first configuration to a second configuration while at least a portion of the cannula is disposed within the vasculature to change an inner diameter of the tubular member.

20 Claims, 20 Drawing Sheets

(56) References Cited

U.S. PATENT DOCUMENTS

| | | | |
|---|---|---|---|
| 5,573,508 A | 11/1996 | Thornton | |
| 5,584,803 A | 12/1996 | Stevens et al. | |
| 5,609,627 A | 3/1997 | Goicoechea et al. | |
| 5,613,980 A | 3/1997 | Chauhan | |
| 5,702,368 A | 12/1997 | Stevens et al. | |
| 5,720,735 A | 2/1998 | Dorros | |
| 5,769,812 A | 6/1998 | Stevens et al. | |
| 5,785,686 A | 7/1998 | Runge | |
| 5,792,094 A | 8/1998 | Stevens et al. | |
| 5,885,238 A | 3/1999 | Stevens et al. | |
| 5,916,193 A | 6/1999 | Stevens et al. | |
| 5,928,181 A | 7/1999 | Coleman et al. | |
| 5,957,879 A | 9/1999 | Roberts et al. | |
| 6,110,145 A | 8/2000 | Macoviak | |
| 6,117,117 A | 9/2000 | Mauch | |
| 6,152,141 A | 11/2000 | Stevens et al. | |
| 6,161,547 A | 12/2000 | Barbut | |
| 6,190,357 B1 | 2/2001 | Ferrari et al. | |
| 6,210,363 B1 | 4/2001 | Esch et al. | |
| 6,210,380 B1 | 4/2001 | Mauch | |
| 6,258,073 B1 | 7/2001 | Mauch | |
| 6,267,751 B1 | 7/2001 | Mangosong | |
| 6,358,238 B1* | 3/2002 | Sherry | A61M 25/005 |
| | | | 604/524 |
| 6,432,136 B1 | 8/2002 | Weiss et al. | |
| 6,461,327 B1 | 10/2002 | Addis et al. | |
| 6,475,208 B2 | 11/2002 | Mauch | |
| 6,494,875 B1 | 12/2002 | Mauch | |
| 6,508,777 B1 | 1/2003 | Macoviak et al. | |
| 6,582,388 B1 | 6/2003 | Coleman et al. | |
| 6,673,040 B1 | 1/2004 | Samson et al. | |
| 6,682,499 B2 | 1/2004 | Lenker | |
| 6,692,473 B2 | 2/2004 | St. Cyr et al. | |
| 6,726,651 B1 | 4/2004 | Robinson et al. | |
| 6,758,836 B2 | 7/2004 | Zawacki | |
| 6,814,713 B2 | 11/2004 | Aboul-Hosn et al. | |
| 6,837,864 B1 | 1/2005 | Bertolero et al. | |
| 6,878,140 B2 | 4/2005 | Barbut | |
| 6,889,713 B2 | 5/2005 | Navis | |
| 6,902,556 B2 | 6/2005 | Grimes et al. | |
| 6,913,601 B2 | 7/2005 | St. Goar et al. | |
| 7,022,100 B1 | 4/2006 | Aboul-Hosn et al. | |
| 7,025,756 B2 | 4/2006 | Frazier et al. | |
| 7,090,659 B2 | 8/2006 | Aboul-Hosn et al. | |
| 7,229,429 B2 | 6/2007 | Martin et al. | |
| 7,240,677 B2 | 7/2007 | Fox | |
| 7,276,043 B2 | 10/2007 | Heath et al. | |
| 7,338,509 B2 | 3/2008 | Mattison | |
| 7,445,592 B2 | 11/2008 | Pecor | |
| 7,473,239 B2 | 1/2009 | Wang et al. | |
| 7,513,863 B2 | 4/2009 | Bolling et al. | |
| 7,569,029 B2 | 8/2009 | Clark | |
| 7,575,563 B2 | 8/2009 | Appling | |
| 7,604,621 B2 | 10/2009 | Eidenschink | |
| 7,766,853 B2 | 8/2010 | Lane | |
| 7,766,896 B2 | 8/2010 | Kornkven Volk et al. | |
| 7,785,246 B2 | 8/2010 | Aboul-Hosn et al. | |
| 7,799,046 B2 | 9/2010 | White et al. | |
| 7,819,856 B2 | 10/2010 | Bates | |
| 7,824,357 B2 | 11/2010 | Al-Rashdan | |
| 7,875,017 B2 | 1/2011 | Sabbah | |
| 7,879,003 B2 | 2/2011 | Bertolero et al. | |
| 7,896,832 B2 | 3/2011 | Zafirelis et al. | |
| 7,935,102 B2 | 5/2011 | Breznock et al. | |
| 7,951,186 B2 | 5/2011 | Eidenschink et al. | |
| 7,971,850 B2 | 7/2011 | Heim et al. | |
| 7,981,093 B2 | 7/2011 | Schon et al. | |
| 8,029,457 B2 | 10/2011 | Ash et al. | |
| 8,231,519 B2 | 7/2012 | Reichenbach et al. | |
| 8,398,693 B2 | 3/2013 | Weber et al. | |
| 9,782,534 B2 | 10/2017 | Kelly et al. | |
| 9,801,657 B2 | 10/2017 | Furnish et al. | |
| 10,279,101 B2 | 5/2019 | Kelly et al. | |
| 10,603,195 B1* | 3/2020 | Sherburne | A61F 2/9517 |
| 10,695,114 B2 | 6/2020 | Fox | |

| | | | |
|---|---|---|---|
| 2002/0142119 A1 | 10/2002 | Seward et al. | |
| 2003/0004452 A1 | 1/2003 | Lenker | |
| 2003/0138350 A1 | 7/2003 | MacOviak et al. | |
| 2004/0171997 A1 | 9/2004 | Wilson et al. | |
| 2005/0038408 A1 | 2/2005 | Von Segesser | |
| 2005/0054990 A1 | 3/2005 | Graft et al. | |
| 2005/0085761 A1* | 4/2005 | Wang | A61M 25/0029 |
| | | | 604/4.01 |
| 2005/0096609 A1 | 5/2005 | Maginot et al. | |
| 2005/0099261 A1 | 5/2005 | Walak | |
| 2005/0102017 A1* | 5/2005 | Mattison | A61L 31/14 |
| | | | 623/1.11 |
| 2005/0277862 A1 | 12/2005 | Anand | |
| 2005/0279370 A1 | 12/2005 | Aboul-Hosn et al. | |
| 2006/0149187 A1 | 7/2006 | Bertolero et al. | |
| 2006/0184098 A1 | 8/2006 | Bamitz et al. | |
| 2006/0235458 A1* | 10/2006 | Belson | A61M 25/0032 |
| | | | 606/191 |
| 2007/0025868 A1* | 2/2007 | Swayze | F04B 43/08 |
| | | | 417/474 |
| 2007/0027467 A1* | 2/2007 | Ortiz | A61M 29/02 |
| | | | 606/198 |
| 2007/0027519 A1* | 2/2007 | Ortiz | A61F 2/966 |
| | | | 623/1.11 |
| 2007/0038224 A1* | 2/2007 | Ortiz | A61B 17/3421 |
| | | | 606/108 |
| 2007/0106247 A1 | 5/2007 | Burnett et al. | |
| 2007/0129704 A1 | 6/2007 | O'Mahony et al. | |
| 2007/0167925 A1 | 7/2007 | Jacqmein | |
| 2007/0197998 A1 | 8/2007 | Itou et al. | |
| 2007/0219576 A1* | 9/2007 | Cangialosi | A61M 29/02 |
| | | | 606/198 |
| 2007/0244550 A1* | 10/2007 | Eidenschink | B29C 70/882 |
| | | | 623/1.49 |
| 2007/0249909 A1* | 10/2007 | Volk | A61M 25/0043 |
| | | | 600/184 |
| 2007/0265631 A1 | 11/2007 | Fox | |
| 2008/0021417 A1 | 1/2008 | Zawacki et al. | |
| 2008/0108975 A1 | 5/2008 | Appling et al. | |
| 2008/0208133 A1 | 8/2008 | Lieberman et al. | |
| 2008/0215018 A1 | 9/2008 | Duffy et al. | |
| 2009/0005725 A1 | 1/2009 | Shorey | |
| 2009/0069792 A1 | 3/2009 | Frey et al. | |
| 2009/0076482 A1 | 3/2009 | Jonkman | |
| 2009/0088699 A1 | 4/2009 | King et al. | |
| 2009/0124968 A1 | 5/2009 | Goshgarian | |
| 2009/0163864 A1 | 6/2009 | Breznock et al. | |
| 2009/0204083 A1 | 8/2009 | O'Donnell et al. | |
| 2009/0247927 A1 | 10/2009 | Clark | |
| 2009/0247987 A1 | 10/2009 | Chevalier, Jr. et al. | |
| 2009/0312702 A1 | 12/2009 | Holman et al. | |
| 2009/0312710 A1 | 12/2009 | Smith | |
| 2010/0004594 A1 | 1/2010 | Eidenschink | |
| 2010/0010442 A1 | 1/2010 | Shivkumar et al. | |
| 2010/0057020 A1 | 3/2010 | Uretsky | |
| 2010/0233282 A1 | 9/2010 | Mishra | |
| 2010/0261950 A1* | 10/2010 | Lund | A61F 2/0045 |
| | | | 600/30 |
| 2011/0040241 A1 | 2/2011 | Wang et al. | |
| 2011/0190683 A1 | 8/2011 | Gellman et al. | |
| 2011/0245665 A1 | 10/2011 | Nentwick | |
| 2011/0313341 A1 | 12/2011 | Kassab | |
| 2011/0313401 A1 | 12/2011 | Ash et al. | |
| 2012/0165788 A1 | 6/2012 | Burnett et al. | |
| 2013/0066157 A1* | 3/2013 | Guralnik | A61B 17/3439 |
| | | | 600/204 |
| 2013/0296885 A1* | 11/2013 | Desai | A61B 17/3417 |
| | | | 606/130 |
| 2014/0012281 A1* | 1/2014 | Wang | A61M 25/0023 |
| | | | 606/108 |
| 2014/0328999 A1* | 11/2014 | Aizenberg | B05D 3/207 |
| | | | 427/547 |
| 2016/0278825 A1 | 9/2016 | Fox | |
| 2017/0143938 A1* | 5/2017 | Ogle | A61B 17/22 |
| 2018/0078698 A1* | 3/2018 | Olaf | A61M 1/3659 |
| 2018/0318077 A1 | 11/2018 | Ness et al. | |
| 2019/0255245 A1 | 8/2019 | Kelly | |
| 2021/0260265 A1 | 8/2021 | Edwards | |

(56)  References Cited

U.S. PATENT DOCUMENTS

| | | | |
|---|---|---|---|
| 2022/0000613 A1* | 1/2022 | Kalfa | A61F 2/2433 |
| 2023/0116901 A1* | 4/2023 | Conlon | A61B 17/221 |
| | | | 606/127 |
| 2023/0240873 A1* | 8/2023 | Erickson | A61M 25/104 |
| | | | 606/1 |

* cited by examiner

DIMENSIONALLY ADJUSTABLE EXTRACORPOREAL LIFE SUPPORT CANNULA

TECHNICAL FIELD

The present disclosure relates generally to systems for extracorporeal life support (ECLS) and/or veno-arterial extracorporeal membrane oxygenation (VA ECMO). More particularly, the present disclosure relates to a cannula for use with extracorporeal life support (ECLS) and/or veno-arterial extracorporeal membrane oxygenation (VA ECMO).

BACKGROUND

Extracorporeal life support (ECLS) and/or veno-arterial extracorporeal membrane oxygenation (VA ECMO) procedures may draw blood from the circulatory system, typically the right atrium, pump the blood through an external oxygenator, and then return the blood into arterial circulation via the pulmonary artery or the femoral artery. These systems are useful for treating patients with right ventricular failure, respiratory failure, or both. In some systems and/or applications, multiple single-lumen cannulas are required. In some systems and/or applications, a dual-lumen cannula may be used.

Patients receiving ECLS and/or VA ECMO may have a wide variety of anatomies and/or sizes. As a result of the wide range of anatomies, there is no "one-size-fits-all" cannula. Hospitals and/or providers must stock many cannulas of the same type in numerous sizes in order to best match the needs of the patient. In some cases, vasculature size is not always known prior to the procedure, such that an improperly sized cannula may be used and then need to be discarded and replaced when the mismatch is discovered.

There is an ongoing need for alternative ECLS and/or VA ECMO devices, components, and/or methods of use and/or manufacture of said devices and/or components.

SUMMARY

An example cannula for an extracorporeal life support system includes a tubular member formed from a polymeric material and having a lumen extending from a proximal end to a distal end and an actuatable structure embedded within the polymeric material. The actuatable structure is responsive to an external stimulus such that an inner diameter of the tubular member changes as the external stimulus changes.

In addition or alternatively to any example described herein, the tubular member is an inner tubular member of a dual lumen cannula.

In addition or alternatively to any example described herein, the tubular member is an outer tubular member of a dual lumen cannula.

In addition or alternatively to any example described herein, the actuatable structure includes a shape memory material.

In addition or alternatively to any example described herein, the tubular member includes a proximal portion having a first outer diameter and a distal portion have a second outer diameter less than the first outer diameter.

In addition or alternatively to any example described herein, the actuatable structure is disposed within the distal portion of the tubular member.

In addition or alternatively to any example described herein, the actuatable structure extends proximally from the distal end of the tubular member.

In addition or alternatively to any example described herein, the external stimulus is an applied voltage.

In addition or alternatively to any example described herein, the external stimulus is temperature.

In addition or alternatively to any example described herein, the external stimulus is light.

Another illustrative example is a system for use with an extracorporeal life support system. The system includes a cannula comprising a tubular member defining a lumen, an actuatable structure fixed to the tubular member, and a controller in electrical communication with the actuatable structure. The actuatable structure is responsive to an applied voltage from the controller such that an inner diameter of the tubular member changes as the applied voltage changes. The controller is user-configurable to set a desired value for an inner diameter of the tubular member. The controller includes a known correlation between the inner diameter of the tubular member and the applied voltage, and the controller is configured to send the applied voltage to the actuatable structure to change the inner diameter of the tubular member to the desired value for the inner diameter.

In addition or alternatively to any example described herein, the inner diameter of the tubular member is expandable in situ.

In addition or alternatively to any example described herein, the inner diameter of the tubular member is collapsible in situ.

In addition or alternatively to any example described herein, the inner diameter of a distal portion of the tubular member is adjustable between about 2 mm and about 10.7 mm.

In addition or alternatively to any example described herein, a portion of the tubular member is devoid of the actuatable structure.

In addition or alternatively to any example described herein, the portion of the tubular member devoid of the actuatable structure is configured to be disposed outside of a patient's body.

Yet another illustrative embodiment is a method of connecting a patient's vasculature to an extracorporeal life support system. The method includes advancing a delivery sheath into the patient's vasculature. The delivery sheath has a cannula comprising a tubular member defining a lumen and an actuatable structure fixed to the tubular member disposed therein. The method further includes moving the delivery sheath relative to the cannula to expose the cannula within the patient's vasculature, and shifting the actuatable structure from a first configuration to a second configuration while at least a portion of the cannula is disposed within the patient's vasculature to change an inner diameter of the tubular member.

In addition or alternatively to any example described herein, shifting the actuatable structure includes applying an external stimulus to the actuatable structure.

In addition or alternatively to any example described herein, the external stimulus is applied by a controller in electrical communication with the actuatable structure.

In addition or alternatively to any example described herein, the method further includes removing the delivery sheath, and fluidly connecting the cannula to the extracorporeal life support system.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
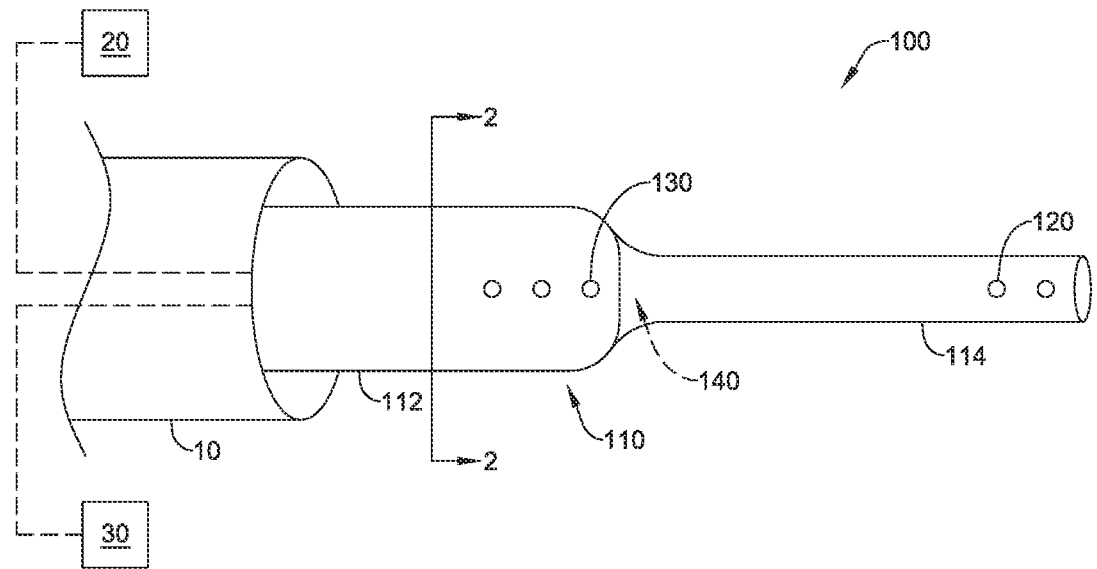
FIG. 1 schematically illustrates selected aspects of a system and cannula for use with an extracorporeal life support system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate example embodiments of the disclosure but not limit the disclosure. Those skilled in the art will recognize that the various elements described and/or shown may be arranged in various combinations and configurations without departing from the scope of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

As used herein, the term "at least one of" is synonymous with "one or more of", and those terms may be used interchangeably. For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

In any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

FIG. 1 schematically illustrates selected aspects of a system for use with an extracorporeal life support (ECLS) system 20. In some embodiments, the system may include a cannula 100 comprising a tubular member 110 defining a lumen extending from a proximal end to a distal end. The ECLS system 20 may be configured to be fluidly connected to the cannula 100 and/or the tubular member 110. In some embodiments, the system may optionally include a delivery sheath 10 having a lumen extending therein. The cannula 100 and/or the tubular member 110 may be slidably receivable within the lumen of the delivery sheath 10, where present.

In at least some embodiments, the tubular member 110 may be formed from a polymeric material. In some embodiments, the tubular member 110 may include a distal end that is open, having an opening extending into a lumen of the tubular member 110. In some embodiments, the tubular member 110 may include a distal end that is closed. In some embodiments, the tubular member 110 may include a first plurality of apertures 120 extending through a wall of the tubular member 110 proximal of and/or adjacent to the distal end which are in fluid communication with a lumen of the tubular member 110. In some embodiments, the tubular member 110 may include a second plurality of apertures 130 extending through the wall of the tubular member 110 proximal of the first plurality of apertures 120 which are in fluid communication with a lumen of the tubular member 110. The second plurality of apertures 130 may be in communication with the same lumen as the first plurality of apertues 120, or the second plurality of apertures 130 may be in fluid communication with a different lumen than the lumen that the first plurality of apertures are in fluid communication with. In some embodiments, a thickness of the wall of the tubular member 110 may be substantially fixed and/or may remain substantially constant.

In some embodiments, the system and/or the cannula 100 may include an actuatable structure 140 fixed (e.g., fixedly attached, fixedly secured, bonded, formed with, embedded in, etc.) to the tubular member 110. In some embodiments, the actuatable structure 140 may be fixed (e.g., fixedly attached, fixedly secured, bonded, formed with, embedded in, etc.) to an outer surface of the tubular member 110. In some embodiments, the actuatable structure 140 may be fixed (e.g., fixedly attached, fixedly secured, bonded, formed with, embedded in, etc.) to an inner surface of the tubular member 110. In some embodiments, the actuatable structure 140 may be at least partially embedded within the tubular member 110 and/or the polymeric material. In some embodiments, the actuatable structure 140 may be completely embedded within the tubular member 110 and/or the polymeric material. Other configurations are also contemplated. Some configurations of the actuatable structure 140 are described in more detail herein.

In some embodiments, the tubular member 110 may include a proximal portion 112 having a first outer diameter and/or a first inner diameter, and a distal portion 114 having a second outer diameter and/or a second inner diameter. In some embodiments, the second outer diameter may be less than the first outer diameter. In some embodiments, the second inner diameter may be less than the first inner diameter. Other configurations are also contemplated. In some embodiments, the tubular member 110 may be tapered between the proximal portion 112 and the distal portion 114 such that the first outer diameter tapers radially inward in a distal direction to the second outer diameter and/or that the first inner diameter tapers radially inward in a distal direction to the second inner diameter. Other configurations are also contemplated.

In some embodiments, a portion of the length of the tubular member 110 may be devoid of the actuatable structure 140. In some embodiments, the portion of the length of the tubular member 110 devoid of the actuatable structure 140 may be configured to be disposed outside of a patient's body. In some embodiments, the portion of the length of the tubular member 110 devoid of the actuatable structure 140 may be the proximal portion 112. In some embodiments, the actuatable structure 140 may be disposed along and/or within the distal portion 114 of the tubular member 110 configured to be inserted into the body of a patient. In some embodiments, the actuatable structure 140 may extend proximally from the distal end of the tubular member 110 along a distal end region of the tubular member 110. In some embodiments, the portion of the length of the tubular member 110 devoid of the actuatable structure 140 may be the distal portion 114. In some embodiments, the actuatable structure 140 may be disposed along and/or within the proximal portion 112 of the tubular member 110. In some embodiments, the actuatable structure 140 may be disposed along and/or within at least a portion of the distal portion 114 and may be disposed along and/or within the proximal portion 112 of the tubular member 110. In some embodiments, the actuatable structure 140 may be disposed along and/or within at least a portion of the distal portion 114 and may be disposed along and/or within at least a portion of the proximal portion 112 of the tubular member 110. Other configurations are also contemplated.

In some embodiments, the actuatable structure 140 may be configured to shift from a first configuration to a second configuration. In some embodiments, the first configuration may be a delivery configuration and the second configuration may be a deployed configuration.

In some embodiments, the actuatable structure 140 may be responsive to an external stimulus such that the inner diameter and/or the outer diameter of the tubular member 110 changes as the external stimulus changes. In some embodiments, the actuatable structure 140 may be configured to shift from the first configuration and/or the delivery configuration to the second configuration and/or the deployed configuration in response to the external stimulus. In some embodiments, the actuatable structure 140 may include a shape memory material (e.g., a shape memory alloy, a shape memory polymer, etc.). In some embodiments, the external stimulus may be an applied voltage. In some embodiments, the external stimulus may be temperature. In some embodiments, the applied voltage to and/or current flow within the actuatable structure 140 may result in a change in temperature within the actuatable structure 140. In some embodiments, the external stimulus may be a light. Other configurations and/or stimuli are also contemplated.

In some embodiments, the system may include a controller 30 in electrical communication with the actuatable structure 140. In some embodiments, the controller 30 may be user-configurable to set or select a desired value for an inner diameter of the tubular member 110. In some embodiments, the controller 30 may be user-configurable to set or select a first desired value for the first inner diameter of the tubular member 110. In some embodiments, the controller 30 may be user-configurable to set or select a second desired value for the second inner diameter of the tubular member 110. In some embodiments, the controller 30 may be user-configurable to set or select a first desired value for the first inner diameter of the tubular member 110 and a second desired value for the second inner diameter of the tubular member 110. Other configurations are also contemplated.

In some embodiments, the actuatable structure 140 may be responsive to an applied voltage from the controller 30 such that the actuatable structure 140 shifts from the first configuration and/or the delivery configuration to the second configuration and/or the deployed configuration. In some embodiments, the actuatable structure 140 may be responsive to the applied voltage from the controller 30 such that the inner diameter of the tubular member 110 changes as the applied voltage changes. The controller 30 may be configured to send the applied voltage to the actuatable structure 140 to change the inner diameter of the tubular member 110 to the desired value for the inner diameter. As discussed herein, in some embodiments, the inner diameter of the tubular member 110 may be expandable in situ and/or the inner diameter of the tubular member 110 may be collapsible in situ. In some embodiments, the controller 30 and/or the desired value for the inner diameter may be changed during the procedure and/or while the cannula 100 and/or the tubular member 110 is disposed in situ.

In some embodiments, the actuatable structure 140 may be responsive to the applied voltage from the controller 30 such that the first inner diameter of the tubular member 110 changes as the applied voltage changes. The controller 30 may be configured to send the applied voltage to the actuatable structure 140 to change the first inner diameter of the tubular member 110 to the first desired value for the first inner diameter. As discussed herein, in some embodiments, the first inner diameter of the tubular member 110 may be expandable in situ and/or the first inner diameter of the tubular member 110 may be collapsible in situ. In some embodiments, the controller 30 and/or the first desired value for the first inner diameter may be changed during the procedure and/or while the cannula 100 and/or the tubular member 110 is disposed in situ.

In some embodiments, the actuatable structure 140 may be responsive to the applied voltage from the controller 30 such that the second inner diameter of the tubular member 110 changes as the applied voltage changes. The controller 30 may be configured to send the applied voltage to the actuatable structure 140 to change the second inner diameter of the tubular member 110 to the second desired value for the second inner diameter. As discussed herein, in some embodiments, the second inner diameter of the tubular member 110 may be expandable in situ and/or the second inner diameter of the tubular member 110 may be collapsible in situ. In some embodiments, the controller 30 and/or the second desired value for the second inner diameter may be changed during the procedure and/or while the cannula 100 and/or the tubular member 110 is disposed in situ.

In some embodiments, the inner diameter of the distal portion 114 of the tubular member 110 and/or the second inner diameter of the tubular member 110 may be adjustable between about 1 millimeter and about 12 millimeters. In some embodiments, the inner diameter of the distal portion 114 of the tubular member 110 and/or the second inner diameter of the tubular member 110 may be adjustable between about 2 millimeters and about 10.7 millimeters. In some embodiments, the inner diameter of the distal portion 114 of the tubular member 110 and/or the second inner diameter of the tubular member 110 may be adjustable between about 3 millimeters and about 9 millimeters. Other configurations are also contemplated.

In some embodiments, the actuatable structure 140 may be responsive to the applied voltage from the controller 30 such that the first inner diameter of the tubular member 110 and the second inner diameter of the tubular member 110 both change as the applied voltage changes. The controller 30 may be configured to send the applied voltage to the actuatable structure 140 to change the first inner diameter of the tubular member 110 to the first desired value for the first inner diameter and the second inner diameter of the tubular member 110 to the second desired value for the second inner diameter.

In some embodiments, the controller 30 may include a known correlation between the inner diameter of the tubular member 110 and the applied voltage. In some embodiments, the known correlation may be stored within the controller 30 in a look-up table and/or algorithm. In some embodiments, the controller 30 may include a plurality of known correlations corresponding to a range of possible values for the desired value of the inner diameter. As such, a user may set or select the desired value for the inner diameter, and the controller 30 may be configured to check the desired value against the look-up table and/or algorithm, and as long as the desired value is within the range of possible values, the controller 30 may automatically send the applied voltage corresponding to the desired value to the actuatable structure 140, which will then cause the inner diameter of the tubular member 110 to change via shifting the actuatable structure 140 from the first configuration and/or the delivery configuration to the second configuration and/or the deployed configuration.

Figure 2A:
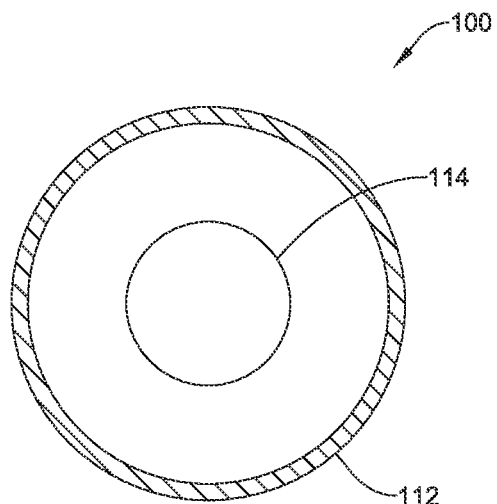
FIG. 2A is a cross-sectional view illustrating selected aspects of the cannula of FIG. 1 configured as a single lumen cannula.
Figure 2B:
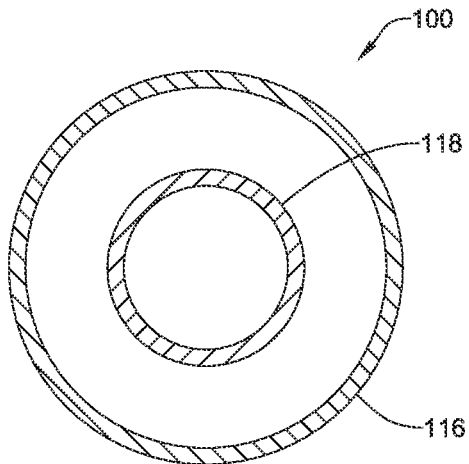
FIG. 2B is a cross-sectional view illustrating selected aspects of the cannula of FIG. 1 configured as a dual lumen cannula.

In some embodiments, the cannula 100 may be a single lumen cannula including the proximal portion 112 and the distal portion 114, as shown in FIG. 2A, having a single lumen extending therethrough. The apertures 120 and/or the apertures 130 may be in fluid communication with the single lumen. In some embodiments, the cannula 100 may be a dual lumen cannula including an inner tubular member 118 and an outer tubular member 116, as shown in FIG. 2B, having a first lumen defined by the inner tubular member 118 and a second lumen defined between the inner tubular member 118 and the outer tubular member 116. In some instances, the inner tubular member 118 may be coaxial with the outer tubular member 116. In some embodiments, the tubular member 110 may be the inner tubular member 118 of the dual lumen cannula. In some embodiments, the tubular member 110 may be the outer tubular member 116 of the dual lumen cannula and/or the cannula 100. In some embodiments, the distal portion 114 may be a distal portion of the inner tubular member 118 of the dual lumen cannula and the proximal portion 112 may be a distal portion of an outer tubular member 116 of the dual lumen cannula and/or the cannula 100. The apertures 120 may be in fluid communication with the first lumen defined by the inner tubular member 118, and the apertures 130 may be in fluid communication with the second lumen defined between the inner tubular member 118 and the outer tubular member 116. In some embodiments, discussion related to the proximal portion 112 may be directed to a proximal portion of the inner tubular member 118 of the dual lumen cannula and/or the cannula 100. Other configurations are also contemplated.

FIGS. 3-8 schematically illustrate the cannula 100 and/or the tubular member 110 undergoing various optional shifts of the actuatable structure 140 between the first configuration and/or the delivery configuration to the second configuration and/or the deployed configuration. In FIGS. 3-9, the cannula 100 is illustrated as a dual lumen cannula with the inner tubular member shown in phantom, but the cannula 100 may be understood to be a single lumen cannula (devoid of the inner tubular member), wherein the figures illustrate various changes to the tubular member, except for FIGS. 6, 7, and 9, which illustrate changes to the inner tubular member of the dual lumen cannula.

Figure 3:
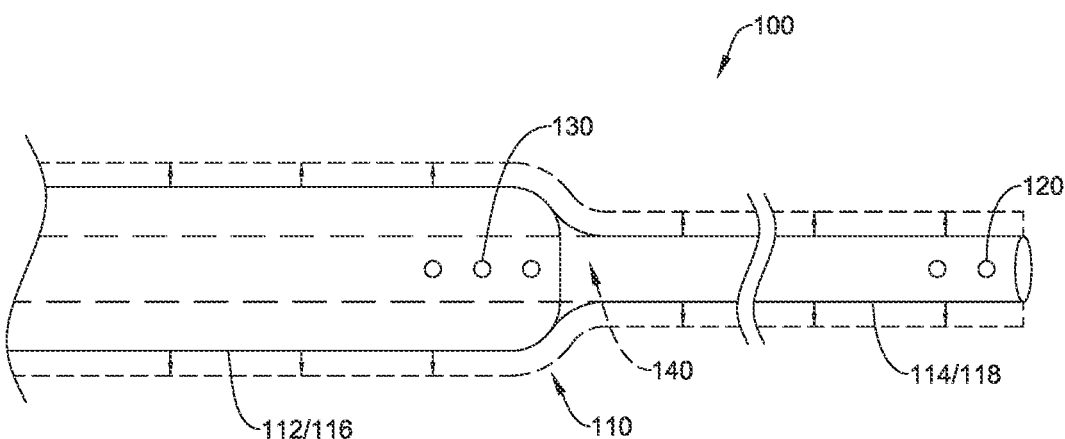
FIGS. 3-9 schematically illustrate selected aspects of the cannula of FIG. 1.

As seen in FIG. 3, in some embodiments of the single lumen cannula, the actuatable structure 140 may be configured to radially expand in response to the external stimulus and/or the applied voltage such that the inner diameter and/or the outer diameter of the tubular member 110 radially expands. In some embodiments of the single lumen cannula, as the actuatable structure 140 shifts from the first configuration and/or the delivery configuration to the second configuration and/or the deployed configuration, the inner diameter and/or the outer diameter of the tubular member 110 radially expands. In some embodiments of the single lumen cannula, as the actuatable structure 140 shifts from the first configuration and/or the delivery configuration to the second configuration and/or the deployed configuration, the inner diameter and/or the outer diameter of both the proximal portion 112 of the tubular member 110 and the distal portion 114 of the tubular member 110 radially expands. In some embodiments of the single lumen cannula, the actuatable structure may extend along both the proximal portion 112 of the tubular member 110 and the distal portion 114 of the tubular member 110. In some embodiments of the single lumen cannula, the first plurality of apertures 120 and/or the second plurality of apertures 130 may be present or may be omitted. Where present, the first plurality of apertures 120 and/or the second plurality of apertures 130 may provide fluid communication between the lumen of the tubular member 110 and an exterior of the cannula 100 and/or the body lumen in which the cannula 100 has been placed. Radially expanding the inner diameter and/or the outer diameter of the tubular member 110 in situ may permit greater fluid flow through the cannula 100 while having a reduced size and/or cross-section for insertion into the body lumen. Other benefits, including but not limited to an improved seal at an access site or puncture and/or maintaining patency of the body lumen, are also contemplated.

As also seen in FIG. 3, in some embodiments of the dual lumen cannula, the actuatable structure 140 may be configured to radially expand in response to the external stimulus and/or the applied voltage such that the inner diameter and/or the outer diameter of at least the distal portion of the outer tubular member 116 radially expands, and/or the inner diameter and/or the outer diameter of the distal portion of the inner tubular member 118 radially expands. In some embodiments of the dual lumen cannula, as the actuatable structure 140 shifts from the first configuration and/or the delivery configuration to the second configuration and/or the deployed configuration, the inner diameter and/or the outer diameter of at least the distal portion of the outer tubular member 116 radially expands, and/or the inner diameter and/or the outer diameter of the distal portion of the inner tubular member 118 radially expands. In some embodiments of the dual lumen cannula, the actuatable structure may extend along at least the distal portion of the outer tubular member 116 and the distal portion of the inner tubular member 118. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and the exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially expanding the inner diameter and/or the outer diameter of the tubular member 110 in situ may permit greater fluid flow through the cannula 100 while having a reduced size and/or cross-section for insertion into the body lumen. Other benefits, including but not limited to an improved seal at an access site or puncture and/or maintaining patency of the body lumen, are also contemplated.

Figure 4:
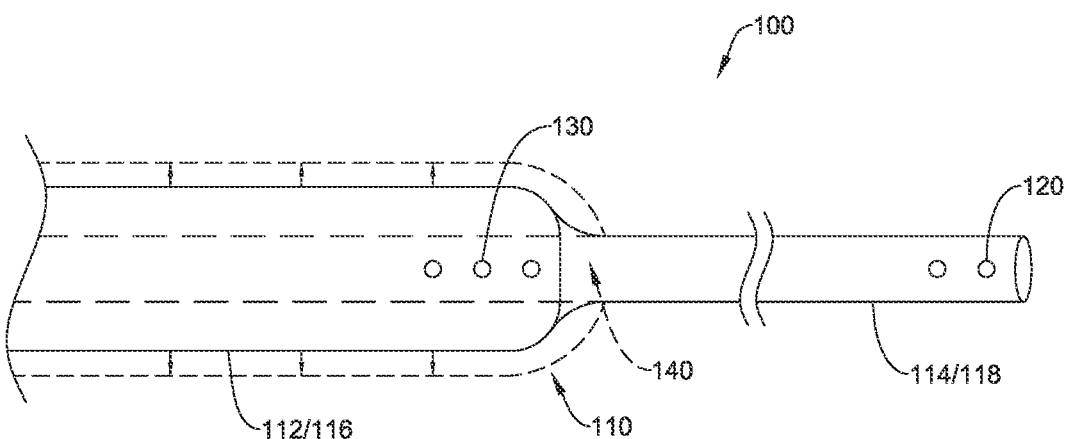

As seen in FIG. 4, in some embodiments of the single lumen cannula, the actuatable structure 140 may be configured to radially expand in response to the external stimulus and/or the applied voltage such that the first inner diameter and/or the first outer diameter of the proximal portion 112 of the tubular member 110 radially expands. In some embodiments of the single lumen cannula, as the actuatable structure 140 shifts from the first configuration and/or the delivery configuration to the second configuration and/or the deployed configuration, the first inner diameter and/or the first outer diameter of the proximal portion 112 of the tubular member 110 radially expands. In some embodiments of the single lumen cannula, as the actuatable structure 140 shifts from the first configuration and/or the delivery configuration to the second configuration and/or the deployed configuration, the first inner diameter and/or the first outer diameter of the proximal portion 112 of the tubular member 110 radially expands, and the second inner diameter and/or the second outer diameter of the distal portion 114 of the tubular member 110 remains constant or generally constant. In some embodiments of the single lumen cannula, the actuatable structure 140 may extend along the proximal portion 112 of the tubular member 110 and the distal portion 114 of the tubular member 110 may be devoid of the actuatable structure 140. In some embodiments of the single lumen cannula, the first plurality of apertures 120 and/or the second plurality of apertures 130 may be present or may be omitted. Where present, the first plurality of apertures 120 and/or the second plurality of apertures 130 may provide fluid communication between the lumen of the tubular member 110 and an exterior of the cannula 100 and/or the body lumen in which the cannula 100 has been placed. Radially expanding the first inner diameter and/or the first outer diameter of the proximal portion 112 of the tubular member 110 in situ may permit greater fluid flow through the proximal portion 112 of the tubular member 110 while having a reduced size and/or cross-section for insertion into the body lumen. Other benefits, including but not limited to an improved seal at an access site or puncture and/or maintaining patency of the body lumen, are also contemplated.

As also seen in FIG. 4, in some embodiments of the dual lumen cannula, the actuatable structure 140 may be configured to radially expand in response to the external stimulus and/or the applied voltage such that the inner diameter and/or the outer diameter of at least the distal portion of the outer tubular member 116 radially expands and the inner diameter and/or the outer diameter of the distal portion of the inner tubular member 118 remains constant or generally constant. In some embodiments of the dual lumen cannula, as the actuatable structure 140 shifts from the first configuration and/or the delivery configuration to the second configuration and/or the deployed configuration, the inner diameter and/or the outer diameter of at least the distal portion of the outer tubular member 116 radially expands, and the inner diameter and/or the outer diameter of the distal portion of the inner tubular member 118 remains constant or generally constant. In some embodiments of the dual lumen cannula, the actuatable structure 140 may extend along at least the distal portion of the outer tubular member 116 and the inner tubular member 118 may be devoid of the actuatable structure 140. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and an exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially expanding the inner diameter and/or the outer diameter of at least the distal portion of the outer tubular member 116 in situ may permit greater fluid flow through the proximal portion 112 of the tubular member 110 while having a reduced size and/or cross-section for insertion into the body lumen. Other benefits, including but not limited to an improved seal at an access site or puncture and/or maintaining patency of the body lumen, are also contemplated.

Figure 5:
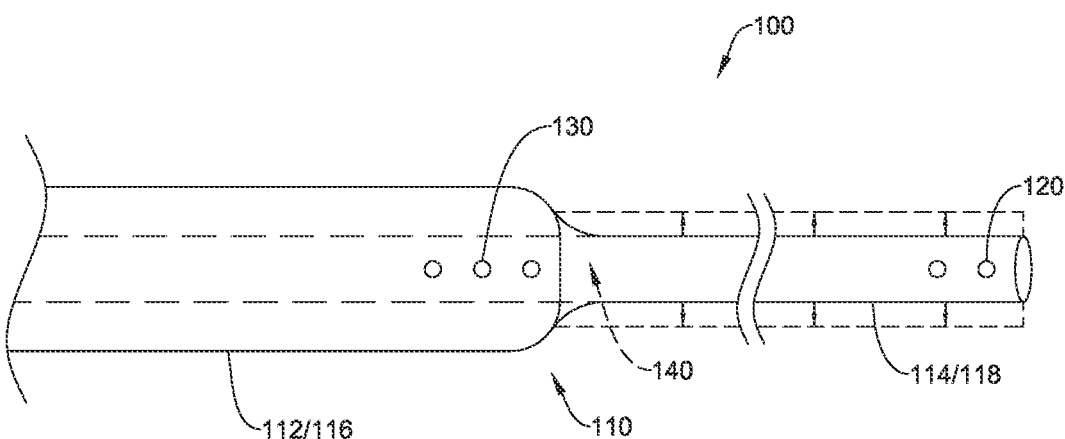

As seen in FIG. 5, in some embodiments of the single lumen cannula, the actuatable structure 140 may be configured to radially expand in response to the external stimulus and/or the applied voltage such that the second inner diameter and/or the second outer diameter of the distal portion 114 of the tubular member 110 radially expands. In some embodiments of the single lumen cannula, as the actuatable structure 140 shifts from the first configuration and/or the delivery configuration to the second configuration and/or the deployed configuration, the second inner diameter and/or the second outer diameter of the distal portion 114 of the tubular member 110 radially expands. In some embodiments of the single lumen cannula, as the actuatable structure 140 shifts from the first configuration and/or the delivery configuration to the second configuration and/or the deployed configuration, the second inner diameter and/or the second outer diameter of the distal portion 114 of the tubular member 110 radially expands, and the first inner diameter and/or the first outer diameter of the proximal portion 112 of the tubular member 110 remains constant or generally constant. In some embodiments of the single lumen cannula, the actuatable structure 140 may extend along the distal portion 114 of the tubular member 110 and the proximal portion 112 of the tubular member 110 may be devoid of the actuatable structure 140. In some embodiments of the single lumen cannula, the first plurality of apertures 120 and/or the second plurality of apertures 130 may be present or may be omitted. Where present, the first plurality of apertures 120 and/or the second plurality of apertures 130 may provide fluid communication between the lumen of the tubular member 110 and an exterior of the cannula 100 and/or the body lumen in which the cannula 100 has been placed. Radially expanding the second inner diameter and/or the second outer diameter of the distal portion 114 of the tubular member 110 in situ may permit greater fluid flow through the distal portion 114 of the tubular member 110 while having a reduced size and/or cross-section for insertion into the body lumen. Other benefits, including but not limited to an improved seal at an access site or puncture and/or maintaining patency of the body lumen, are also contemplated.

As also seen in FIG. 5, in some embodiments of the dual lumen cannula, the actuatable structure 140 may be configured to radially expand in response to the external stimulus and/or the applied voltage such that the inner diameter and/or the outer diameter of the distal portion of the inner tubular member 118 radially expands and the inner diameter and/or the outer diameter of at least the distal portion of the outer tubular member 116 remains constant or generally constant. In some embodiments of the dual lumen cannula, as the actuatable structure 140 shifts from the first configuration and/or the delivery configuration to the second configuration and/or the deployed configuration, the inner diameter and/or the outer diameter of the distal portion of the inner tubular member 118 radially expands, and the inner diameter and/or the outer diameter of at least the distal portion of the outer tubular member 116 remains constant or generally constant. In some embodiments of the dual lumen cannula, the actuatable structure 140 may extend along at least the distal portion of the inner tubular member 118 and the outer tubular member 116 may be devoid of the actuatable structure 140. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and an exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially expanding the inner diameter and/or the outer diameter of the distal portion of the inner tubular member 118 in situ may permit greater fluid flow through the distal portion of the inner tubular member 118 while having a reduced size and/or cross-section for insertion into the body lumen. Other benefits, including but not limited to an improved seal at an access site or puncture and/or maintaining patency of the body lumen, are also contemplated.

Figure 6:
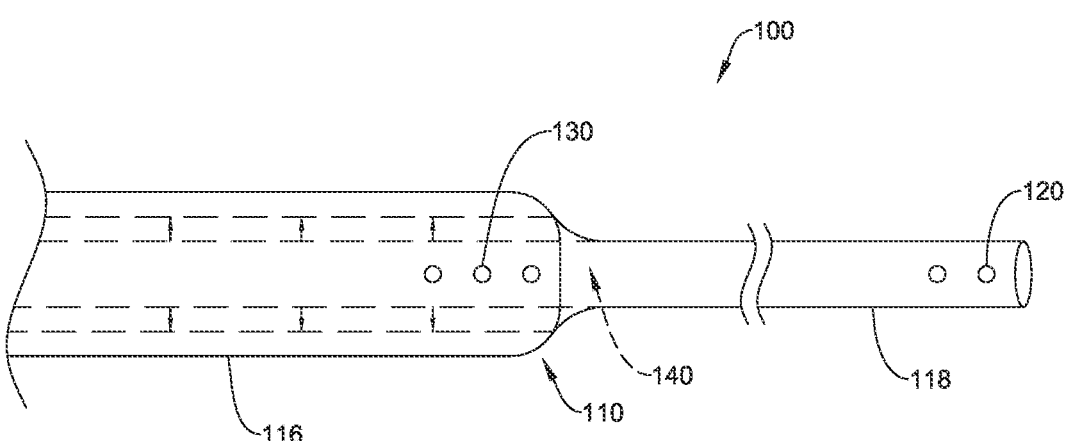

As seen in FIG. 6, in some embodiments of the dual lumen cannula, the actuatable structure 140 may be configured to radially expand in response to the external stimulus and/or the applied voltage such that the inner diameter and/or the outer diameter of a proximal portion of the inner tubular member 118 (e.g., a portion of the inner tubular member 118 disposed proximal of the distal end of the outer tubular member 116) radially expands and the inner diameter and/or the outer diameter of at least the distal portion of the outer tubular member 116 remains constant or generally constant. In some embodiments, the inner diameter and/or the outer diameter of the distal portion of the inner tubular member 118 (e.g., a portion of the inner tubular member 118 disposed distal of the distal end of the outer tubular member 116) remains constant or generally constant. In some embodiments of the dual lumen cannula, as the actuatable structure 140 shifts from the first configuration and/or the delivery configuration to the second configuration and/or the deployed configuration, the inner diameter and/or the outer diameter of the proximal portion of the inner tubular member 118 radially expands, and the inner diameter and/or the outer diameter of at least the distal portion of the outer tubular member 116 remains constant or generally constant. In some embodiments of the dual lumen cannula, the actuatable structure 140 may extend along the proximal portion of the inner tubular member 118 and the outer tubular member 116 may be devoid of the actuatable structure 140. In some embodiments, the distal portion of the inner tubular member 118 may be devoid of the actuatable structure 140. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and an exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially expanding the inner diameter and/or the outer diameter of the proximal portion of the inner tubular member 118 in situ may permit greater fluid flow through the proximal portion of the inner tubular member 118 and/or may reduce fluid flow through at least the distal portion of the outer tubular member 116. In some embodiments, the actuatable structure 140 may be used to control fluid flow within the outer tubular member 116. Other benefits are also contemplated.

Figure 7:
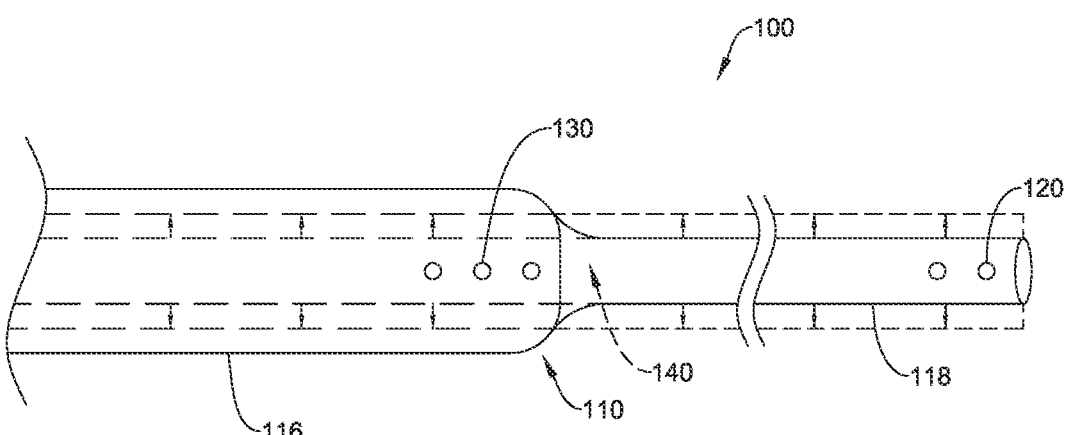

As seen in FIG. 7, in some embodiments of the dual lumen cannula, the actuatable structure 140 may be configured to radially expand in response to the external stimulus and/or the applied voltage such that the inner diameter and/or the outer diameter of the inner tubular member 118 radially expands and the inner diameter and/or the outer diameter of at least the distal portion of the outer tubular member 116 remains constant or generally constant. In some embodiments of the dual lumen cannula, as the actuatable structure 140 shifts from the first configuration and/or the delivery configuration to the second configuration and/or the deployed configuration, the inner diameter and/or the outer diameter of the inner tubular member 118 radially expands, and the inner diameter and/or the outer diameter of at least the distal portion of the outer tubular member 116 remains constant or generally constant. In some embodiments of the dual lumen cannula, the actuatable structure 140 may extend along the proximal portion and the distal portion of the inner tubular member 118 and the outer tubular member 116 may be devoid of the actuatable structure 140. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and an exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially expanding the inner diameter and/or the outer diameter of the inner tubular member 118 in situ may permit greater fluid flow through the inner tubular member 118 and/or may reduce fluid flow through at least the distal portion of the outer tubular member 116. In some embodiments, the actuatable structure 140 may be used to control fluid flow within the outer tubular member 116 and/or the inner tubular member 118. In some embodiments, radially expanding the inner diameter and/or the outer diameter of the inner tubular member 118 in situ may permit greater fluid flow through the inner tubular member 118 while having a reduced size and/or cross-section for insertion of at least the distal portion of the inner tubular member 118 into the body lumen. Other benefits, including but not limited to an improved seal at an access site or puncture and/or maintaining patency of the body lumen, are also contemplated.

Figure 8:
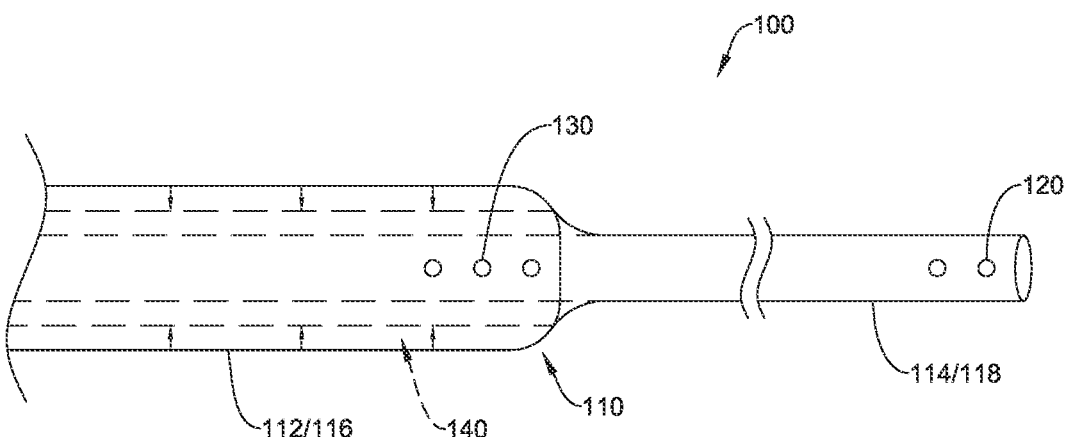

As seen in FIG. 8, in some embodiments of the single lumen cannula, the actuatable structure 140 may be configured to radially collapse in response to the external stimulus and/or the applied voltage such that the first inner diameter and/or the first outer diameter of the proximal portion 112 of the tubular member 110 radially collapses. In some embodiments of the single lumen cannula, as the actuatable structure 140 shifts from the first configuration and/or the delivery configuration to the second configuration and/or the deployed configuration, the first inner diameter and/or the first outer diameter of the proximal portion 112 of the tubular member 110 radially collapses. In some embodiments of the single lumen cannula, as the actuatable structure 140 shifts from the first configuration and/or the delivery configuration to the second configuration and/or the deployed configuration, the first inner diameter and/or the first outer diameter of the proximal portion 112 of the tubular member 110 radially collapses, and the second inner diameter and/or the second outer diameter of the distal portion 114 of the tubular member 110 remains constant or generally constant. In some embodiments of the single lumen cannula, the actuatable structure 140 may extend along the proximal portion 112 of the tubular member 110 and the distal portion 114 of the tubular member 110 may be devoid of the actuatable structure 140. In some embodiments of the single lumen cannula, the first plurality of apertures 120 and/or the second plurality of apertures 130 may be present or may be omitted. Where present, the first plurality of apertures 120 and/or the second plurality of apertures 130 may provide fluid communication between the lumen of the tubular member 110 and an exterior of the cannula 100 and/or the body lumen in which the cannula 100 has been placed. Radially collapsing the first inner diameter and/or the first outer diameter of the proximal portion 112 of the tubular member 110 in situ may reduce fluid flow through the proximal portion 112 of the tubular member 110. In some embodiments, the actuatable structure 140 may be used to control fluid flow within the tubular member 110 and/or within the proximal portion 112 of the tubular member 110. Other benefits are also contemplated.

As also seen in FIG. 8, in some embodiments of the dual lumen cannula, the actuatable structure 140 may be configured to radially collapse in response to the external stimulus and/or the applied voltage such that the inner diameter and/or the outer diameter of at least the distal portion of the outer tubular member 116 radially collapses and the inner diameter and/or the outer diameter of the inner tubular member 118 remains constant or generally constant. In some embodiments of the dual lumen cannula, as the actuatable structure 140 shifts from the first configuration and/or the delivery configuration to the second configuration and/or the deployed configuration, the inner diameter and/or the outer diameter of at least the distal portion of the outer tubular member 116 radially collapses, and the inner diameter and/or the outer diameter of the inner tubular member 118 remains constant or generally constant. In some embodiments of the dual lumen cannula, the actuatable structure 140 may extend along at least the distal portion of the outer tubular member 116 and the inner tubular member 118 may be devoid of the actuatable structure 140. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and an exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially collapsing the inner diameter and/or the outer diameter of at least the distal portion of the outer tubular member 116 in situ may reduce fluid flow through at least the distal portion of the outer tubular member 116. In some embodiments, the actuatable structure 140 may be used to control fluid flow within the outer tubular member 116. Other benefits are also contemplated.

Figure 9:
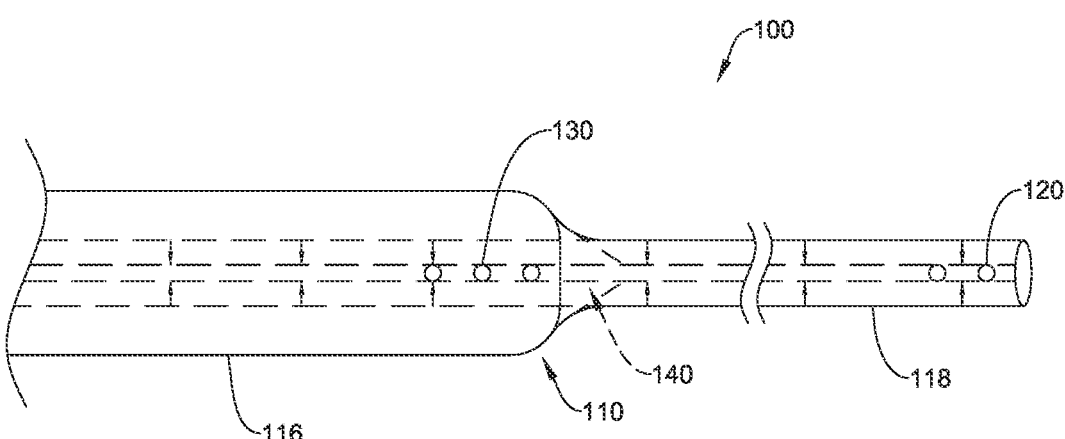

As seen in FIG. 9, in some embodiments of the dual lumen cannula, the actuatable structure 140 may be configured to radially collapse in response to the external stimulus and/or the applied voltage such that the inner diameter and/or the outer diameter of the inner tubular member 118 radially collapses and the inner diameter and/or the outer diameter of at least the distal portion of the outer tubular member 116 remains constant or generally constant. In some embodiments of the dual lumen cannula, as the actuatable structure 140 shifts from the first configuration and/or the delivery configuration to the second configuration and/or the deployed configuration, the inner diameter and/or the outer diameter of the inner tubular member 118 radially collapses, and the inner diameter and/or the outer diameter of at least the distal portion of the outer tubular member 116 remains constant or generally constant. In some embodiments of the dual lumen cannula, the actuatable structure 140 may extend along the proximal portion and the distal portion of the inner tubular member 118 and the outer tubular member 116 may be devoid of the actuatable structure 140. In some embodiments of the dual lumen cannula, the first plurality of apertures 120 and/or the second plurality of apertures 130 may be present or may be omitted. Where present, the first plurality of apertures 120 may provide fluid communication between the lumen of the inner tubular member 118 and an exterior of the cannula 100 and/or the body lumen in which the cannula 100 has been placed, and the second plurality of apertures 130 may provide fluid communication between the lumen of the outer tubular member 116 and the exterior of the cannula 100 and/or the body lumen in which the cannula 100 has been placed. Radially collapsing the inner diameter and/or the outer diameter of the inner tubular member 118 in situ may reduce fluid flow through the inner tubular member 118 and/or may increase fluid flow through at least the distal portion of the outer tubular member 116. In some embodiments, the actuatable structure 140 may be used to control fluid flow within the outer tubular member 116 and/or the inner tubular member 118. Other benefits are also contemplated.

Figure 10:
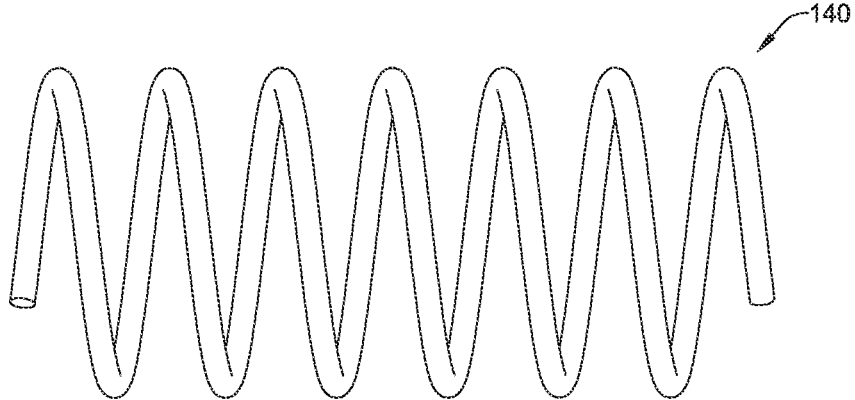
FIGS. 10, 10A, and 10B illustrates selected aspects of an actuatable structure according to the disclosure.
Figure 10A:
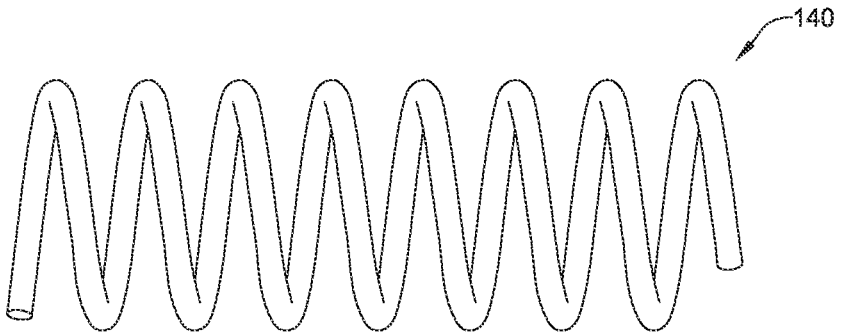
Figure 10B:
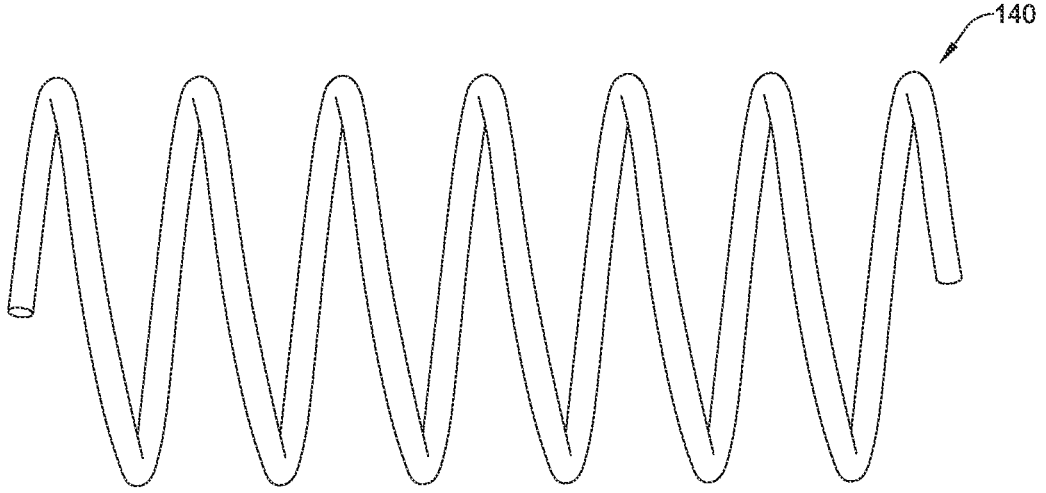

FIG. 10 illustrates one example configuration for the actuatable structure 140. In some embodiments, the actuatable structure 140 may include and/or may be a helical coil. The actuatable structure 140 is illustrated in FIG. 10 in the first configuration and/or the delivery configuration. In some embodiments, the actuatable structure 140 and/or the helical coil may include a plurality of adjacent windings. The plurality of adjacent windings may be spaced apart generally uniformly along the length of the actuatable structure 140 and/or the helical coil. In some embodiments, the plurality of adjacent windings may be spaced apart by varying distances along the length of the actuatable structure 140 and/or the helical coil. Other configurations are also contemplated. FIG. 10A illustrates one example of the actuatable structure 140 of FIG. 10 in the second configuration and/or the deployed configuration. In some embodiments, in the second configuration and/or the deployed configuration, the actuatable structure 140 may be radially collapsed compared to the first configuration and/or the delivery configuration. FIG. 10B illustrates another example of the actuatable structure 140 of FIG. 10 in the second configuration and/or the deployed configuration. In some embodiments, in the second configuration and/or the deployed configuration, the actuatable structure 140 may be radially expanded compared to the first configuration and/or the delivery configuration. In some embodiments, the actuatable structure 140 may be progressive such that the second configuration and/or the delivery configuration depends and/or varies based on the external stimulus the actuatable structure 140 is subjected to, as discussed herein.

Figure 11:
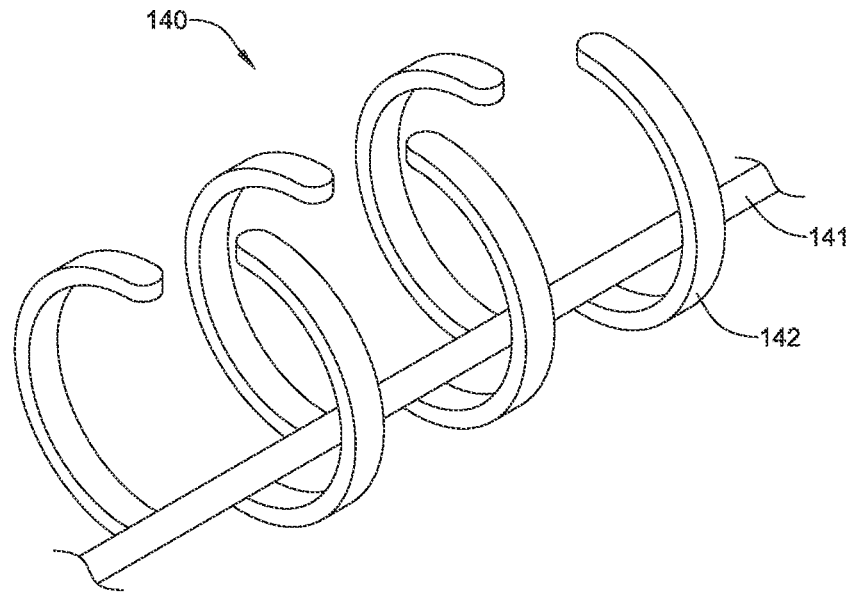
FIGS. 11, 11A, and 11B illustrates selected aspects of an actuatable structure according to the disclosure.
Figure 11A:
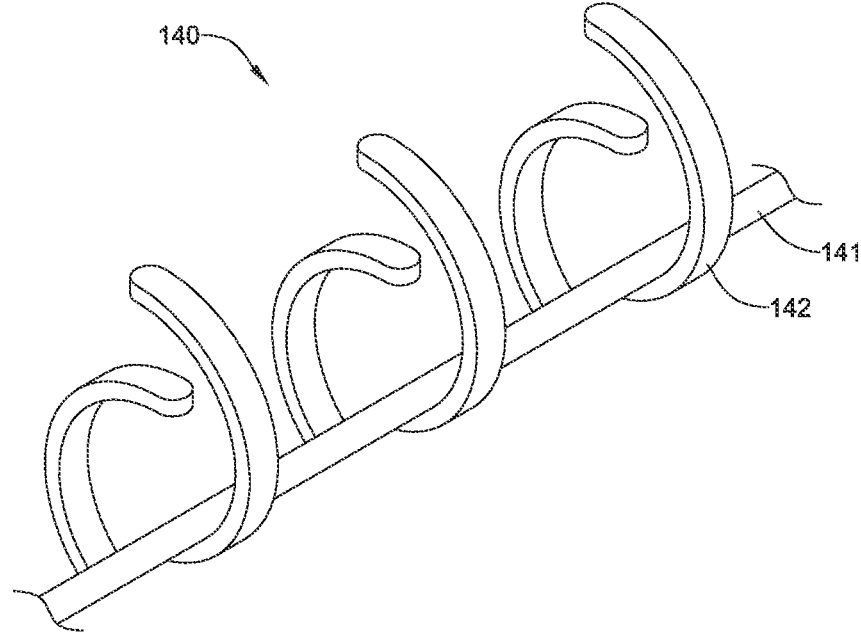
Figure 11B:
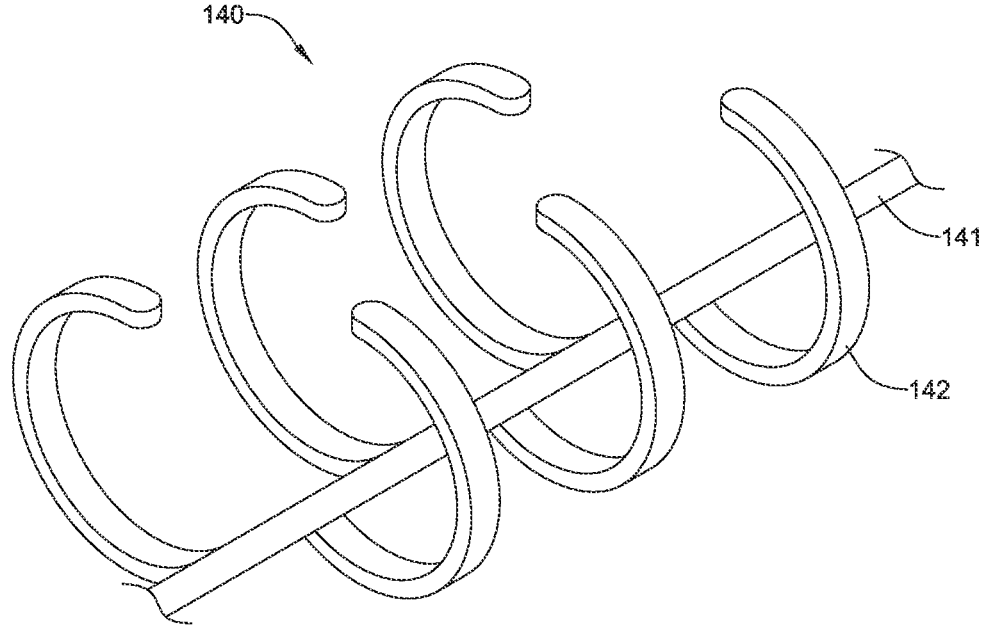

FIG. 11 illustrates another example configuration for the actuatable structure 140. In some embodiments, the actuatable structure 140 may include and/or may be a cage-like structure (e.g., a rib cage, etc.). The actuatable structure 140 is illustrated in FIG. 11 in the first configuration and/or the delivery configuration. In some embodiments, the actuatable structure 140 and/or the cage-like structure may include a plurality of curved ribs 142 extending from a longitudinal spine 141. In some embodiments, the plurality of curved ribs 142 may extend in an arcuate direction from the longitudinal spine 141. In some embodiments, the plurality of curved ribs 142 may extend circumferentially from the longitudinal spine 141. In some embodiments, a first portion of the plurality of curved ribs 142 may extend from the longitudinal spine 141 in a first arcuate direction from a first side of the longitudinal spine 141, and a second portion of the plurality of curved ribs 142 may extend from the longitudinal spine 141 in a second arcuate direction from a second side of the longitudinal spine 141. The first arcuate direction and/or first side may be opposite the second arcuate direction and/or second side. In some embodiments, the plurality of curved ribs 142 may extend alternatingly from opposite sides of the longitudinal spine 141. In other words, the direction the curved ribs 142 extend from the longitudinal spine 141 may alternate along the length of the longitudinal spine 141. In at least some embodiments, the plurality of curved ribs 142 may be monolithically formed with and/or may be unitary with the longitudinal spine 141. In some embodiments, the plurality of curved ribs 142 may be configured to deflect and/or pivot at and/or about the longitudinal spine 141 as the actuatable structure 140 and/or the cage-like structure shifts from the first configuration and/or the delivery configuration to the second configuration and/or the deployed configuration. The plurality of curved ribs 142 may be spaced apart generally uniformly along the length of the actuatable structure 140 and/or the cage-like structure. In some embodiments, the plurality of curved ribs 142 may be spaced apart by varying distances along the length of the actuatable structure 140 and/or the cage-like structure. In some instances the longitudinal spacing between adjacent curved ribs 142 may gradually increase in the distal direction, or the longitudinal spacing between adjacent curved ribs 142 may gradually decrease in the distal direction, if desired. Other configurations are also contemplated. FIG. 11A illustrates one example of the actuatable structure 140 of FIG. 11 in the second configuration and/or the deployed configuration. In some embodiments, in the second configuration and/or the deployed configuration, the actuatable structure 140 may be radially collapsed compared to the first configuration and/or the delivery configuration. FIG. 11B illustrates another example of the actuatable structure 140 of FIG. 11 in the second configuration and/or the deployed configuration. In some embodiments, in the second configuration and/or the deployed configuration, the actuatable structure 140 may be radially expanded compared to the first configuration and/or the delivery configuration. In some embodiments, the actuatable structure 140 may be progressive such that the second configuration and/or the delivery configuration depends and/or varies based on the external stimulus the actuatable structure 140 is subjected to, as discussed herein.

Figure 12:
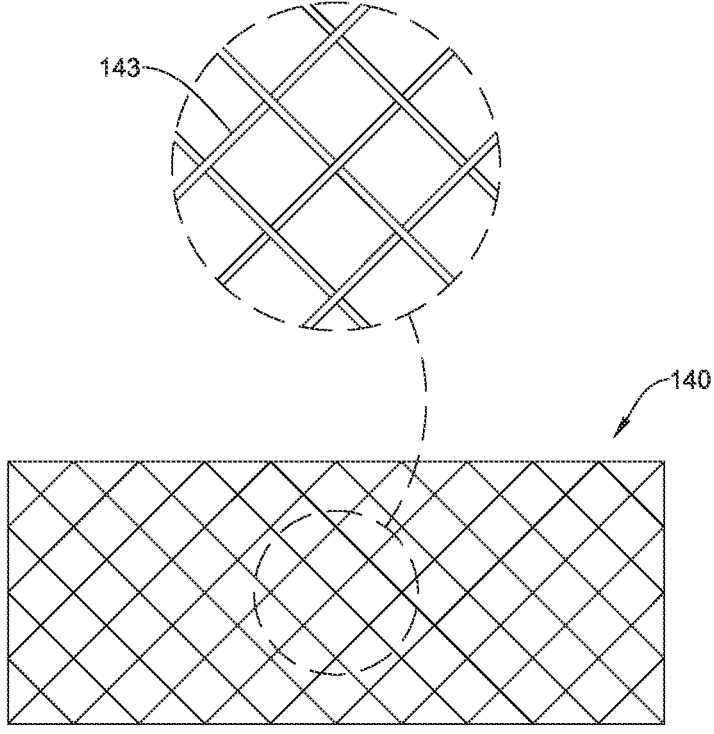
FIGS. 12, 12A, and 12B illustrates selected aspects of an actuatable structure according to the disclosure.
Figure 12A:
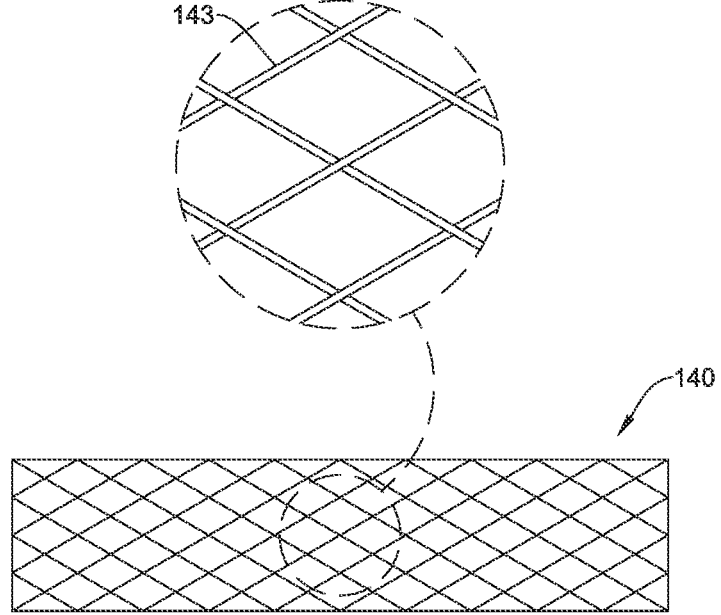
Figure 12B:
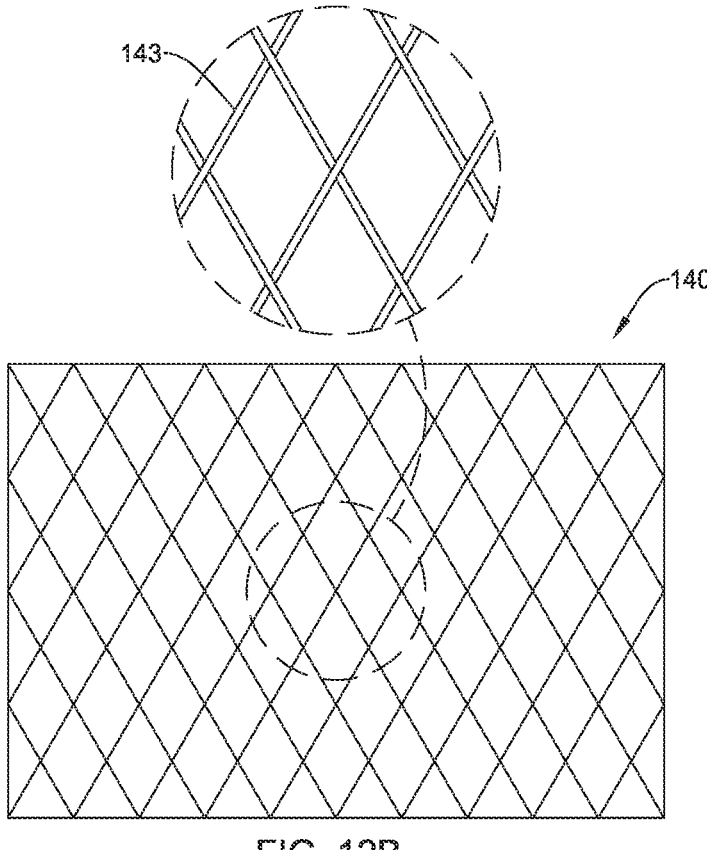

FIG. 12 illustrates another example configuration for the actuatable structure 140. In some embodiments, the actuatable structure 140 may include and/or may be a braided stent-like structure. The actuatable structure 140 is illustrated in FIG. 12 in the first configuration and/or the delivery configuration. In some embodiments, the actuatable structure 140 and/or the braided stent-like structure may include a plurality of interwoven filaments 143. In some embodiments, the plurality of interwoven filaments 143 may be configured to move relative to each other as the actuatable structure 140 and/or the braided stent-like structure shifts from the first configuration and/or the delivery configuration to the second configuration and/or the deployed configuration. Other configurations are also contemplated. FIG. 12A illustrates one example of the actuatable structure 140 of FIG. 12 in the second configuration and/or the deployed configuration. In some embodiments, in the second configuration and/or the deployed configuration, the actuatable structure 140 may be radially collapsed and/or longitudinally elongated compared to the first configuration and/or the delivery configuration. FIG. 12B illustrates another example of the actuatable structure 140 of FIG. 12 in the second configuration and/or the deployed configuration. In some embodiments, in the second configuration and/or the deployed configuration, the actuatable structure 140 may be radially expanded and/or longitudinally shortened compared to the first configuration and/or the delivery configuration. In some embodiments, the actuatable structure 140 may be progressive such that the second configuration and/or the delivery configuration depends and/or varies based on the external stimulus the actuatable structure 140 is subjected to, as discussed herein.

Figure 13:
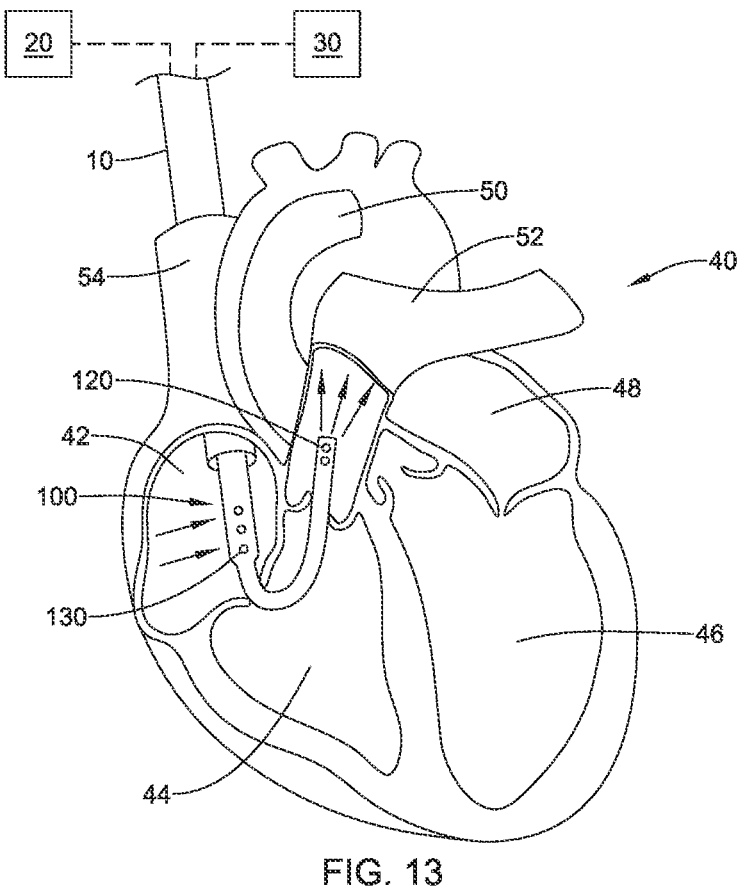
FIG. 13 is a partial cutaway view illustrating selected aspects related to a method of using the system and cannula of FIG. 1.

In some embodiments, a method of connecting a patient's vasculature to the extracorporeal life support (ECLS) system 20 may comprise advancing the delivery sheath 10 into the patient's vasculature. The patient's vasculature may include one or more of the patient's arteries, veins, and/or heart. FIG. 13 illustrates one example configuration and/or placement of the cannula 100 within the patient's vasculature in relation to the heart 40. For the purpose of illustration, the heart 40 includes the right atrium 42, the right ventricle 44, the left ventricle 46, and the left atrium 48. The left ventricle 46 is fluidly connected to the aorta and the right ventricle 44 is fluidly connected to the pulmonary artery 52. It shall be understood that the cannula 100 may be disposed and/or placed within other portions of the patient's vasculature as is known in the art.

As discussed herein, the delivery sheath 10 may have the cannula 100 comprising the tubular member 110 defining a lumen and the actuatable structure 140 fixed to the tubular member 110 disposed therein. In some embodiments, the cannula 100 may be a single lumen cannula as described herein. In some embodiments, the cannula 100 may be a dual lumen cannula as described herein.

In some embodiments, the method may include advancing the delivery sheath 10 into and/or through the superior vena cava 54 and into the right atrium 42. In some embodiments, the delivery sheath 10 may be advanced into and/or through the right ventricle 44 and into the pulmonary artery 52. In some embodiments, the method may include moving the delivery sheath 10 relative to the cannula 100 to expose the cannula 100 within the patient's vasculature. In the example configuration of FIG. 13, the method may include moving the delivery sheath 10 relative to the cannula 100 to expose the cannula 100 within the patient's heart 40. In some embodiments, the method may include retracting the delivery sheath 10 relative to the cannula 100 while the cannula 100 is held in a generally constant position relative to the patient's vasculature. In some embodiments, the method may include advancing the cannula 100 out of the distal end of the delivery sheath 10 while the delivery sheath 10 is held in a generally constant position relative to the patient's vasculature.

In some embodiments, the method may include shifting the actuatable structure 140 from the first configuration and/or the delivery configuration to the second configuration and/or the deployed configuration while at least a portion of the cannula 100 is disposed within the patient's vasculature to change the inner diameter and/or the outer diameter of the tubular member 110.

In some embodiments of the single lumen cannula, the method may include shifting the actuatable structure 140 from the first configuration and/or the delivery configuration to the second configuration and/or the deployed configuration while at least a portion of the cannula 100 is disposed within the patient's vasculature to change the first inner diameter and/or the first outer diameter of proximal portion 112 of the tubular member 110. In some embodiments of the single lumen cannula, the method may include shifting the actuatable structure 140 from the first configuration and/or the delivery configuration to the second configuration and/or the deployed configuration while at least a portion of the cannula 100 is disposed within the patient's vasculature to change the second inner diameter and/or the second outer diameter of distal portion 114 of the tubular member 110. In some embodiments of the single lumen cannula, the method may include shifting the actuatable structure 140 from the first configuration and/or the delivery configuration to the second configuration and/or the deployed configuration while at least a portion of the cannula 100 is disposed within the patient's vasculature to change the first inner diameter and/or the first outer diameter of proximal portion 112 of the tubular member 110 and the second inner diameter and/or the second outer diameter of distal portion 114 of the tubular member 110.

In some embodiments of the dual lumen cannula, the method may include shifting the actuatable structure 140 from the first configuration and/or the delivery configuration to the second configuration and/or the deployed configuration while at least a portion of the cannula 100 is disposed within the patient's vasculature to change the inner diameter and/or the outer diameter of at least a portion of the inner tubular member 118. In some embodiments of the dual lumen cannula, the method may include shifting the actuatable structure 140 from the first configuration and/or the delivery configuration to the second configuration and/or the deployed configuration while at least a portion of the cannula 100 is disposed within the patient's vasculature to change the inner diameter and/or the outer diameter of at least a portion of the outer tubular member 116. In some embodiments of the dual lumen cannula, the method may include shifting the actuatable structure 140 from the first configuration and/or the delivery configuration to the second configuration and/or the deployed configuration while at least a portion of the cannula 100 is disposed within the patient's vasculature to change the inner diameter and/or the outer diameter of at least a portion of the inner tubular member 118 and at least a portion of the outer tubular member 116.

In some embodiments, shifting the actuatable structure 140 from the first configuration and/or the delivery configuration to the second configuration and/or the deployed configuration while at least a portion of the cannula 100 is disposed within the patient's vasculature may include applying an external stimulus to the actuatable structure 140. In some embodiments, the external stimulus may be applied by the controller 30. The controller 30 may be in electronic and/or electrical communication with the actuatable structure 140. In some embodiments, the external stimulus may be applied to the actuatable structure 140 actively and/or selectively (e.g., an applied voltage). In some embodiments, the external stimulus may be applied passively (e.g., body heat). In some embodiments, the external stimulus may include a plurality of stimuli.

In some embodiments, the method may include removing the delivery sheath 10 from the patient's vasculature. In some embodiments, the method may include fluidly connecting the cannula 100 to the extracorporeal life support (ECLS) system 20. In some embodiments, the method may include fluidly connecting the cannula 100 to the extracorporeal life support (ECLS) system 20 using means, methods, and/or techniques known in the art.

In some embodiments, such as in a dual lumen cannula, the second plurality of apertures 130 may be in fluid communication with the extracorporeal life support (ECLS) system 20 and may be configured to provide fluid outflow from the patient's vasculature (e.g., the right atrium 42, etc.) to the extracorporeal life support (ECLS) system via the outer tubular member 116, and/or the first plurality of apertures 120 may be in fluid communication with the extracorporeal life support (ECLS) system 20 and may be configured to provide fluid inflow into the patient's vasculature (e.g., the pulmonary artery 52, etc.) from the extracorporeal life support (ECLS) system 20 via the inner tubular member 118, as shown using arrows in FIG. 13. Other configurations are also contemplated. For example, in a single lumen cannula, the first plurality of apertures 120 and/or the second plurality of apertures 130, where present, may be configured to provide fluid outflow from the patient's vasculature to the extracorporeal life support (ECLS) system 20. In another example, in a single lumen cannula, the first plurality of apertures 120 and/or the second plurality of apertures 130, where present, may be configured to provide fluid inflow from the extracorporeal life support (ECLS) system 20 to the patient's vasculature.

The materials that can be used for the various components of the cannula and the various elements thereof disclosed herein may include those commonly associated with medical devices. For simplicity purposes, the following discussion refers to the device. However, this is not intended to limit the devices, components, and methods described herein, as the discussion may be applied to other elements, members, components, or devices disclosed herein, such as, but not limited to, the delivery sheath, the tubular member, the inner tubular member, the outer tubular member, the actuatable structure, etc. and/or elements or components thereof.

In some embodiments, the device and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, ether or ester based copolymers (for example, butylene/poly (alkylene ether) phthalate and/or other polyester elastomers), polyamide, elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12, perfluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbonates, polyisobutylene (PIB), polyisobutylene polyurethane (PIBU), polyurethane silicone copolymers, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; or any other suitable material.

In some embodiments, the device and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryroyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, antiplatelet receptor antibodies, aspirin, prostaglandin inhibitors, platelet inhibitors, and tick antiplatelet peptides (TAP)); vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A cannula for an extracorporeal life support system, comprising:
   a tubular member formed from a polymeric material and having a lumen extending from a proximal end to a distal end; and
   an actuatable structure embedded within the polymeric material;
   wherein the actuatable structure is responsive to an external stimulus such that an inner diameter of the tubular member changes and an outer circumferential surface of the tubular member changes uniformly as the external stimulus changes;
   wherein the inner diameter is adjustable to be maintained at one or more diameters between a first inner diameter and a second inner diameter via an amount of the external stimulus applied to the actuatable structure, the first inner diameter being less than the second inner diameter.

2. The cannula of claim 1, wherein the tubular member is an inner tubular member of a dual lumen cannula.

3. The cannula of claim 1, wherein the tubular member is an outer tubular member of a dual lumen cannula.

4. The cannula of claim 1, wherein the actuatable structure includes a shape memory material.

5. The cannula of claim 1, wherein the tubular member includes a proximal portion having a first outer diameter and a distal portion have a second outer diameter less than the first outer diameter.

6. The cannula of claim 5, wherein the actuatable structure is disposed within the distal portion of the tubular member.

7. The cannula of claim 6, wherein the actuatable structure extends proximally from the distal end of the tubular member.

8. The cannula of claim 1, wherein the external stimulus is an applied voltage.

9. The cannula of claim 1, wherein the external stimulus is temperature.

10. The cannula of claim 1, wherein the external stimulus is light.

11. The cannula of claim 1, wherein the actuatable structure comprises a plurality of curved ribs extending from a longitudinal spine.

12. A system for use with an extracorporeal life support system, comprising:
   a cannula comprising a tubular member defining a lumen;
   an actuatable structure embedded within a polymeric material of the tubular member; and
   a controller in electrical communication with the actuatable structure;
   wherein the actuatable structure is responsive to an applied voltage from the controller such that an inner diameter of the tubular member changes and an outer circumferential surface of the tubular member changes uniformly as the applied voltage changes;
   wherein the controller is user-configurable to set a desired value for an inner diameter of the tubular member at one or more selected diameters between a first inner diameter and a second inner diameter via an amount of the applied voltage, the first inner diameter being less than the second inner diameter;
   wherein the controller includes a known correlation between the selected inner diameter of the tubular member and the applied voltage, and the controller is configured to send the applied voltage to the actuatable structure to change the inner diameter of the tubular member to the selected inner diameter between the first inner diameter and the second inner diameter.

13. The system of claim 12, wherein the inner diameter of the tubular member is expandable in situ.

14. The system of claim 12, wherein the inner diameter of the tubular member is collapsible in situ.

15. The system of claim 12, wherein the inner diameter of a distal portion of the tubular member is adjustable between about 2 mm and about 10.7 mm.

16. The system of claim 12, wherein a portion of the tubular member is devoid of the actuatable structure.

17. The system of claim 16, wherein the portion of the tubular member devoid of the actuatable structure is configured to be disposed outside of a patient's body.

18. The system of claim 12, wherein the actuatable structure comprises a plurality of curved ribs extending from a longitudinal spine.

19. A method of connecting a patient's vasculature to an extracorporeal life support system, comprising:
   advancing a delivery sheath into the patient's vasculature, the delivery sheath having a cannula slidably positioned therewithin, the cannula comprising a tubular member defining a lumen and an actuatable structure embedded with a polymeric material of the tubular member, wherein the actuatable structure is responsive to an applied voltage to adjust and maintain an inner diameter of the tubular member to one or more selected diameters between a first inner diameter and a second inner diameter, the first inner diameter being less than the second inner diameter;

moving the delivery sheath relative to the cannula to expose the cannula within the patient's vasculature; and applying a voltage to the actuatable structure via a controller to shift the actuatable structure from a first configuration to a second configuration while at least a portion of the cannula is disposed within the patient's vasculature to change the inner diameter of the tubular member to one of the one or more selected diameters between the first inner diameter and the second inner diameter while an outer circumferential surface of the tubular member changes uniformly;

wherein the controller is configured to maintain the inner diameter of the tubular member at the one of the one or more selected diameters.

20. The method of claim 19, wherein the actuatable structure comprises a plurality of curved ribs extending from a longitudinal spine.

\* \* \* \* \*